United States Patent
Reyes et al.

(10) Patent No.: US 12,409,066 B2
(45) Date of Patent: Sep. 9, 2025

(54) MULTI-DIAPHRAGM VITRECTOMY PROBE

(71) Applicant: Alcon Inc., Fribourg (CH)

(72) Inventors: Nathaniel Reyes, Santa Ana, CA (US); Jesus R. Gonzales, Jr., Wernersville, PA (US); Mark W. Vojtasek, Reading, PA (US)

(73) Assignee: Alcon Inc., Fribourg (CH)

( * ) Notice: Subject to any disclaimer, the term of this patent is extended or adjusted under 35 U.S.C. 154(b) by 901 days.

(21) Appl. No.: 17/476,600

(22) Filed: Sep. 16, 2021

(65) Prior Publication Data

US 2022/0104969 A1 Apr. 7, 2022

Related U.S. Application Data

(60) Provisional application No. 63/088,529, filed on Oct. 7, 2020.

(51) Int. Cl.
*A61F 9/007* (2006.01)

(52) U.S. Cl.
CPC .................... *A61F 9/00763* (2013.01)

(58) Field of Classification Search
CPC .. A61F 9/00736; A61F 9/00763; A61B 17/32; A61B 2017/00539; A61B 2017/00544; A61B 2017/00535; A61B 2018/00601; A61B 18/1492; A61B 2218/002; A61B 2218/007; A61B 2218/008

See application file for complete search history.

(56) References Cited

U.S. PATENT DOCUMENTS

| | | | |
|---|---|---|---|
| 4,940,468 A | * | 7/1990 | Petillo ............... A61F 9/00763 604/22 |
| 5,019,035 A | | 5/1991 | Missirlian |
| 5,176,628 A | | 1/1993 | Charles et al. |
| 6,773,445 B2 | | 8/2004 | Finlay |
| 8,038,692 B2 | | 10/2011 | Valencia |
| 8,080,029 B2 | | 12/2011 | Charles |
| 8,187,293 B2 | | 5/2012 | Kirchhevel |
| 8,540,743 B2 | | 9/2013 | Auld |
| 8,545,529 B2 | | 10/2013 | Underwood et al. |
| 9,005,228 B2 | | 4/2015 | Underwood |
| 9,095,409 B2 | | 8/2015 | Underwood |
| 9,101,442 B2 | | 8/2015 | Mcdonell |
| 9,486,360 B2 | | 11/2016 | Chon |

(Continued)

FOREIGN PATENT DOCUMENTS

EP 1810616 A1 7/2007

*Primary Examiner* — Julian W Woo
*Assistant Examiner* — Chima U Igboko
(74) *Attorney, Agent, or Firm* — PATTERSON + SHERIDAN, LLP

(57) ABSTRACT

A diaphragm driven vitrectomy probe employing multiple diaphragms. The probe includes multiple diaphragms providing added areas to which hydraulic air may be delivered in reciprocating a cutter of the probe. Thus, the diaphragms and the probe housing may be reduced in size without sacrifice to force driving cutter reciprocation. Additionally, the amount of force attained and the rate of cutter reciprocation may be increased through the use of multiple diaphragms. Alternatively, the use of added diaphragms may allow for the rate of cutter reciprocation to be maintained even while the air pressure utilized may be reduced.

10 Claims, 6 Drawing Sheets

(56) References Cited

U.S. PATENT DOCUMENTS

| | | |
|---|---|---|
| 9,517,161 B2 | 12/2016 | Underwood |
| 9,974,689 B2 | 5/2018 | Mcdonell |
| 10,111,777 B2 | 10/2018 | Gunn |
| 10,251,782 B2 | 4/2019 | Farley |
| 10,369,046 B2 | 8/2019 | Mcdonell |
| 10,639,197 B2 | 5/2020 | Lopez |
| 10,758,411 B2 | 9/2020 | Dean |
| 10,893,978 B2 | 1/2021 | Sawicz |
| 10,918,411 B2 | 2/2021 | Mcdonell |
| 2008/0029574 A1* | 2/2008 | Shelton ............ A61B 17/07207 227/176.1 |
| 2008/0188881 A1 | 8/2008 | Chon |
| 2009/0082715 A1* | 3/2009 | Charles ............... A61F 9/00763 606/171 |
| 2012/0158030 A1 | 6/2012 | Underwood et al. |
| 2012/0165724 A1* | 6/2012 | Auld ................... A61F 9/00763 604/22 |
| 2013/0150779 A1 | 6/2013 | Field |
| 2018/0243134 A1 | 8/2018 | Dean |
| 2018/0369016 A1 | 12/2018 | Underwood |
| 2019/0000672 A1 | 1/2019 | Mcdonell |
| 2020/0016001 A1 | 1/2020 | Mcdonell |

* cited by examiner

MULTI-DIAPHRAGM VITRECTOMY PROBE

PRIORITY CLAIM

This application claims the benefit of priority of U.S. Provisional Patent Application Ser. No. 63/088,529 titled "MULTI-DIAPHRAGM VITRECTOMY PROBE," filed on Oct. 7, 2020, whose inventors are Nathaniel Reyes, Jesus R. Gonzales, Jr., and Mark Vojtasek, which is hereby incorporated by reference in its entirety as though fully and completely set forth herein.

BACKGROUND

Over the years, many dramatic advancements in the field of eye surgery have taken place. When the eye surgery includes accessing the retina, it is common that a vitrectomy will be included in at least part of the procedure. Vitrectomy is the removal of some or all of the vitreous humor from a patient's eye. In some cases, where the surgery was limited to removal of clouded vitreous humor, the vitrectomy may constitute the majority of the procedure. However, a vitrectomy may accompany surgery to repair a retina, to address a macular pucker, or a host of other issues.

The vitreous humor itself is a clear gel that may be removed by an elongated probe when inserted through a pre-placed cannula at the eye. More specifically, the probe includes a central channel for removal of the vitreous humor. Further, the cannula provides a structurally supportive conduit strategically located at an offset location at the front of the eye, such as the pars plana. In this way, the probe may be guidingly inserted into the eye in a manner that avoids damage to the patient's lens or cornea.

Unfortunately, removal of the vitreous humor requires greater care than simply applying a vacuum through the channel of the probe. This is because the vitreous humor includes a fibrous matrix of collagen fibrils. Therefore, merely applying a vacuum to the gel would place the surrounding eye structure in jeopardy. That is, the fibrous nature of the gel is such that a vacuum pull on the gel into the probe might translate into a pull on the retina, optic nerve or other delicate eye structures.

In order to address this issue, vitrectomy probes are configured to cut vitreous humor as it is drawn into the channel of the probe. In this way, a continuous fibrous pull on the gel-like substance does not translate into a pull on delicate eye structures. Instead, the vitreous humor is pulled into the channel of the probe in very small, chopped segments. This chipping or cutting of the vitreous humor occurs by the reciprocation of a cutter within the channel of the probe. More specifically, the cutter reciprocates back and forth at a port for intake of the vitreous humor in a manner that cuts the substance as it is being drawn into the channel. Perhaps 5,000 to 10,000 cuts per minute may take place in this manner in order to safeguard the eye from pulling by the vitreous humor as it is being removed. In fact, depending on the internal architecture of a reciprocating diaphragm, the cutter may achieve up to 15,000 cuts per minute (or higher). For example, this may be the case where a diaphragm having an effective diameter of a little over 0.41 inches is employed. Once more, this may be doubled to about 30,000 cuts per minute (or higher) where a two-way cutter is utilized, wherein each reciprocation results in two cuts, one in each direction of the reciprocation.

Of course, reciprocating a cutter by way of a reciprocating diaphragm that is over about 0.40 inches in effective diameter and accounting for the housing and other architecture built up around the diaphragm, the probe may have an outer diameter that is well over about 0.6 inches, often up to 0.7 inches. By way of comparison, consider a very large sharpie or marker. While the surgeon may prefer the option of tool with a diameter the size of a pencil for sake of added control during a vitrectomy procedure, such an option may simply not be practical due to the underlying size of the diaphragm. Ultimately, the size of the diaphragm presents a design limitation to the probe in terms of final diameter.

Of course, the size of the diaphragm may be reduced in order to reduce the ultimate probe diameter. Indeed, for tools where no diaphragm is required, such as a laser instrument, the diameter is often less than about 0.3 inches, closer to that of a pencil or other precision instrument. However, applying this type of thinking to a vitrectomy probe and minimizing the diaphragm size would result in a reduction in force that the diaphragm is able to impart on the cutter and thus a fairly dramatic reduction in cutter speed. In fact, reducing the size by about 30% would cut the force in half. The end result would be to dramatically reduce the performance of the probe function. Ultimately, with current probe technology, the surgeon is left with either an instrument less capable in terms of performance or a larger diameter instrument which may afford the surgeon less precision.

SUMMARY

A vitrectomy probe is disclosed. The probe includes a first diaphragm and a second diaphragm. Each diaphragm is driven in a first direction and an opposite second direction by hydraulic air that is reciprocatingly delivered to each. In this way, two separate diaphragms in a series are simultaneously employed to reciprocate the same cutting support of the probe during use in a surgical procedure.

BRIEF DESCRIPTION OF THE DRAWINGS

FIG. 4 is schematic view of an embodiment of an architectural layout for the air channels of FIG. 2a.

DETAILED DESCRIPTION

In the following description, numerous details are set forth to provide an understanding of the present disclosure. However, it will be understood by those skilled in the art that the embodiments described may be practiced without these particular details. Further, numerous variations or modifications may be employed which remain contemplated by the embodiments as specifically described.

Embodiments are described with reference to certain types of vitrectomy probe surgical procedures. In particular, a procedure in which vitreous humor is removed to address vitreous hemorrhage is illustrated. However, tools and techniques detailed herein may be employed in a variety of other manners. For example, embodiments of a vitrectomy probe as detailed herein may be utilized to address retinal detachments, macular pucker, macular holes, vitreous floaters, diabetic retinopathy or a variety of other eye conditions. Regardless, so long as the vitrectomy probe incorporates multiple diaphragms in series, appreciable benefit may be realized.

Figure 1:
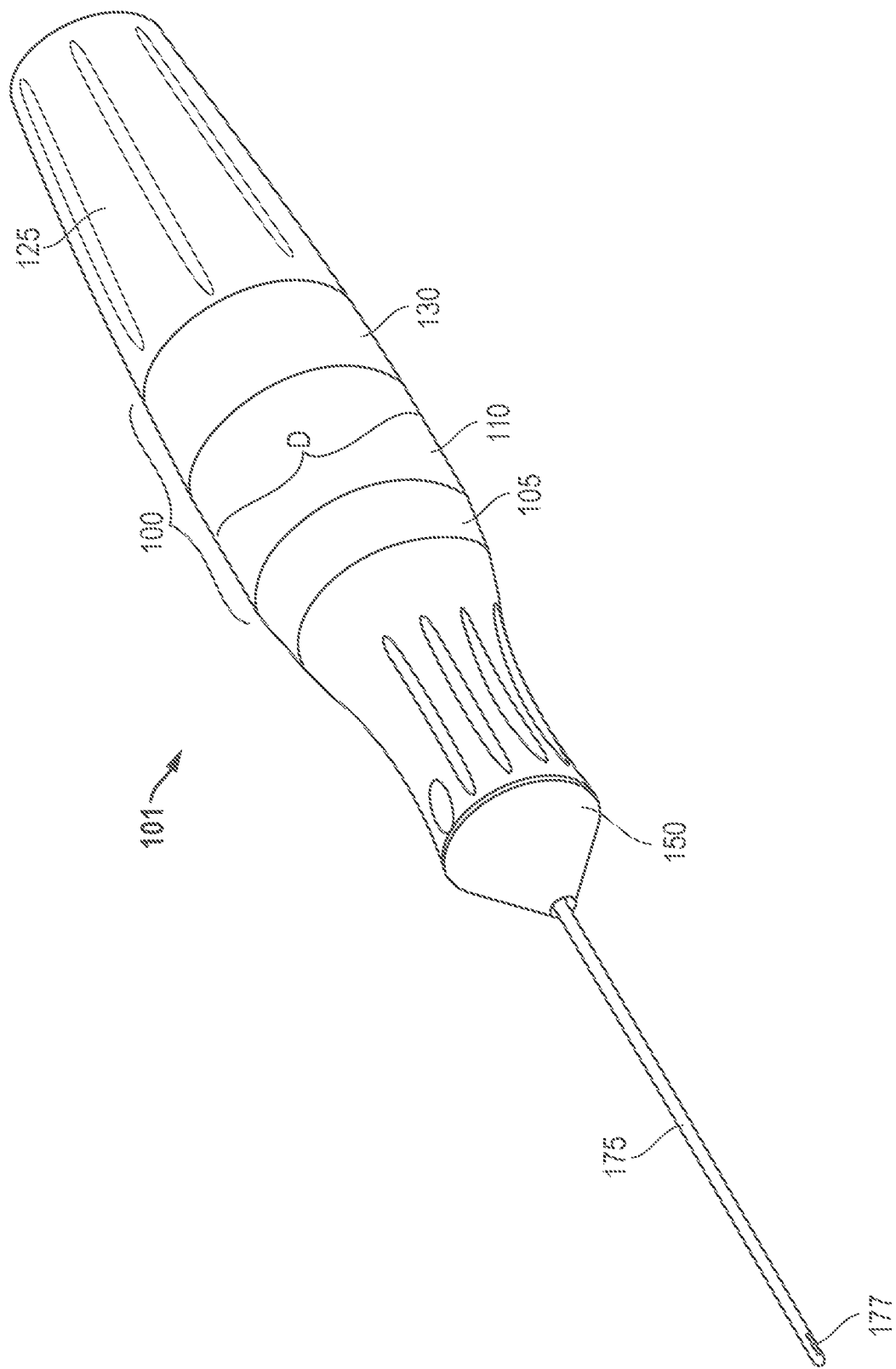
FIG. 1 is a perspective view of an embodiment of a multi-diaphragm vitrectomy probe.

Referring now to FIG. 1, a perspective view of an embodiment of a multi-diaphragm vitrectomy probe 101 is illustrated. The probe 101 includes a component housing 100 that is segmented. Specifically, distal 105, middle 110 and proximal 130 housing segments are illustrated. These segments 105, 110, 130 may or may not be visible from the exterior. For example, with added reference to FIG. 2a, they may be located beneath a housing cover 290. Regardless, the segments 105, 110, 130 are configured to accommodate diaphragms 210, 230 therebetween. Thus, as suggested above, the probe 101 may be referred to as a multi-diaphragm vitrectomy probe 101.

The housing 100 is coupled to a shell 125 which is provided as an ergonomic support for a surgeon employing the probe 101 during a procedure. In absence of the shell 125, the handheld portion of the probe 101 effectively consists of no more than the housing 100 which may be under a few inches in total length. A surgeon may or may not choose to utilize the probe 101 with the shell 125 in place as illustrated. That is, as a matter of user preference, the surgeon may choose to remove the shell 125 for surgery. Thus, the probe 101 is configured such that the shell is removable in a user friendly manner that does not subject the probe 101 to potential damage with the surgeon crudely attempting to pry the shell 125 from the probe 101. In this way, the vitrectomy procedure may be performed with the surgeon holding the end casing 150 solely between a thumb and forefinger without any other interfering support.

Returning to the component housing 100, notice that it is of a given diameter (D). As discussed further below, the diameter (D) may be reduced to a degree depending on the number of segments 105, 110, 130 utilized which is in turn based on the number of diaphragms 210, 230 utilized (see FIG. 2a). For example, in one embodiment, the diameter (D) may be about half an inch while still generating the same force that might result from a conventional component housing that is well in excess of 0.60 inches in diameter. Thus, the probe 101 itself may become thinner and potentially more maneuverable for the surgeon without sacrifice to cut rate or performance. Indeed, the flexibility in design may allow for even greater cut rate and performance such as where more than two diaphragms are utilized or the use of a housing cover 290 of any substantial thickness is avoided (see FIG. 2a). More specific exemplary embodiments and numbers are provided below. Regardless, so long as multiple diaphragms 210, 230 are employed, the probe 101 may be made thinner without any sacrifice to performance, and indeed, performance may even be improved (again see FIG. 2a). Further, to maintain traditional dimensions where the overall probe length from end casing 150 to the opposite end of the shell 125 at about 3 inches or less, the shell 125 may simply be reduced in size as more and more segments 110, 130 are added. In an embodiment where each segment 105, 110, 130 takes up between about 0.1 and 0.3 inches, perhaps up to five segments 105, 110, 130 (e.g. 4 diaphragms) may be utilized without adding to the overall length of the probe 101. Of course, the option of allowing the overall length of the probe 101 to increase may also be viable.

Figure 2A:
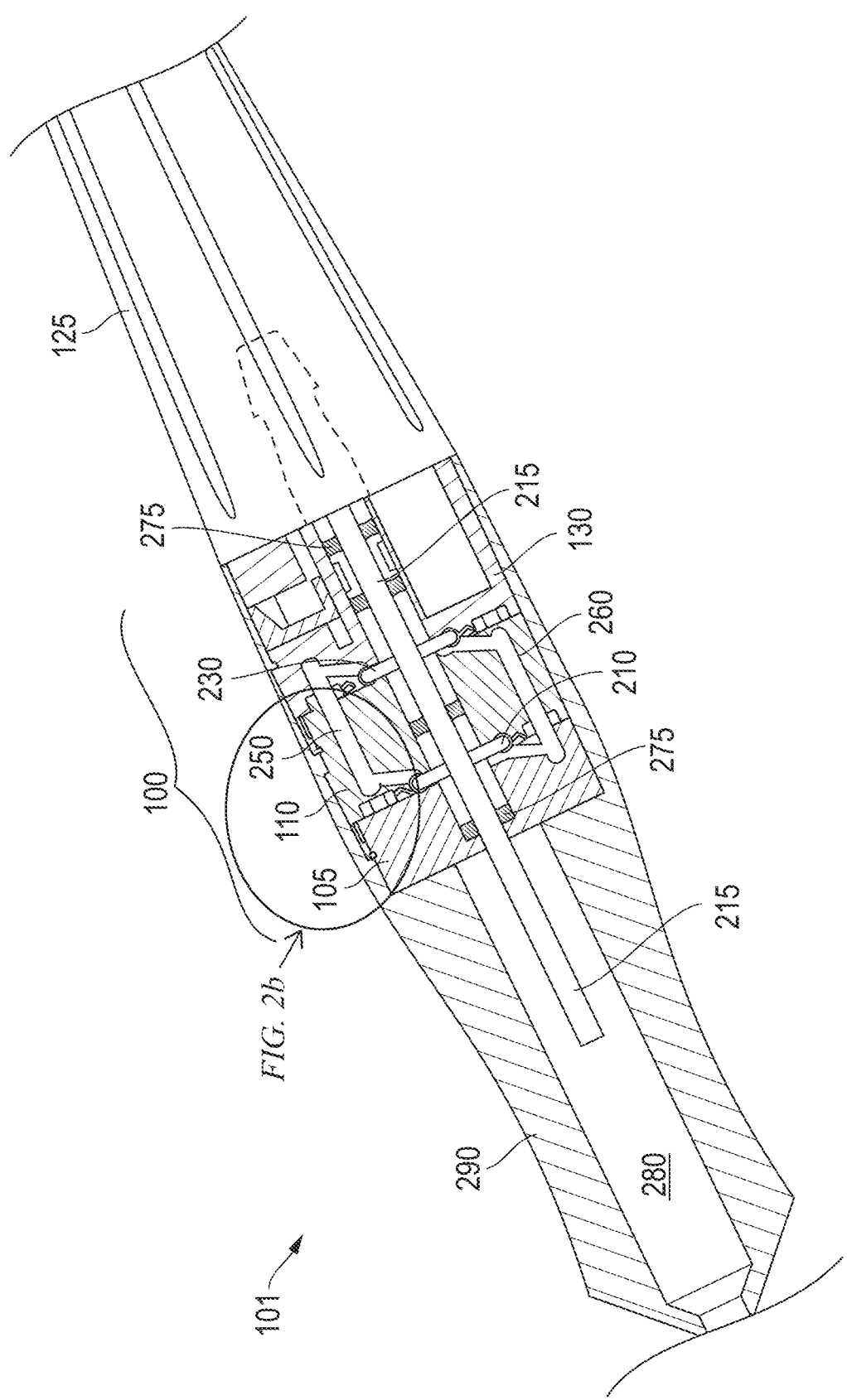
FIG. 2a is cross-sectional view of the multi-diaphragm vitrectomy probe of FIG. 1 revealing unique air channels thereto.

Referring more directly now to FIG. 2a, a cross-sectional view of the multi-diaphragm vitrectomy probe 101 of FIG. 1 is illustrated. In this view, air channels 250, 260 of fairly unique architecture are visible. Specifically, as discussed further below, the front channel 260 is configured to ensure that air directed at the front side of the diaphragms 210, 230 reaches both diaphragms 210, 230 at substantially the same time. Further, the back channel 250 is configured to ensure that air directed at the back side of the diaphragms 210, 230 reaches both diaphragms 210, 230 at substantially the same time.

Air reaching multiple diaphragms 210, 230 simultaneously and in a reciprocating manner reciprocates an extension tube 215 which accommodates the vitreous humor cutter within a passage 280 as referenced above. The force that drives this reciprocation is a combined force obtained from each of the reciprocating diaphragms 210, 230. More specifically, the force generated is equal to the supplied air pressure multiplied by the area for each of the diaphragms 210, 230. So, for example, where 10 psi is applied to a conventional larger diaphragm with a diameter of about 0.41 inches, a force of about 1.32 lbs. might be obtained which might generally translate to between about 10,000-15,000 reciprocations per minute. In other words, $10 \times \pi (0.205)^2$ is 1.32 lbs. This may translate into 20,000-30,000 cuts per minute where the probe employs a double cutter (with cuts in both directions of the reciprocation). Regardless, in the embodiment shown, the diaphragms 210, 230 may be smaller than a conventional diaphragm, perhaps about 0.29 inches in diameter. Ultimately, this may result in a thinner probe 101 as noted above. Nevertheless, because there are multiple diaphragms 210, 230, there need not be any sacrifice to the force attained. More specifically, $10 \times \pi (0.145)^2$ is 0.66 lbs. for each of two diaphragms 210, 230. Thus, 1.32 lbs. of force is still attained in total which should still translate into between about 10,000-15,000 reciprocations per minute.

Of course, the amount of force is not the only factor that determines the reciprocation rate. For example, the extension tube 215 interfaces a variety of seals 275 that are employed to ensure discrete pressure isolation during reciprocation as described. This may affect the rate depending on the degree of force at the interfaces between the seals 275 and the tube 215. However, by way of contrast to a conventional probe 101 with a larger diaphragm, with all other factors such as seal interfacing being the same, the utilization of smaller diaphragms has not sacrificed attainable force nor reciprocation rate such as in the example noted above.

Figure 2B:
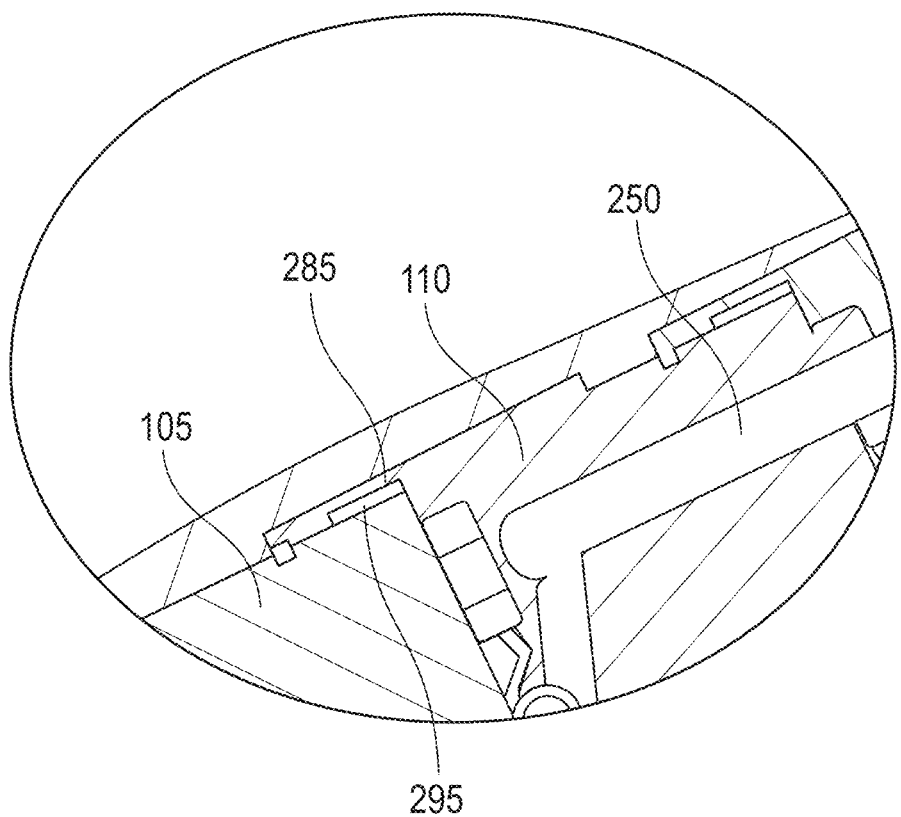
FIG. 2b shows an alternate configuration for using snap fitting for connecting segments of the vitrectomy probe together.

Continuing with reference to FIG. 2a, note the modular nature of the probe housing 100. In some embodiments, the segments 105, 110, 130 may be secured through a friction fit and/or adhesive for a smooth interface between the segments (e.g., as seen in FIG. 2a). In an alternate embodiment, the segments 105, 110, 130 are of an architecture for snap-fitting or mechanically keying together (e.g., as seen in the alternate embodiment shown in FIG. 2b). In some embodiments, the snap-fitting and/or mechanical keying of the different segments may be used along with, for example, adhesive (or other connection mechanisms) for a stronger bond between the sections. For example, snaps 285 may extend from one section and snap into an adjacent section. The material for the snap 285 may be the same material as the section it extends from and may be resilient enough to hold downward pressure on a keying feature at the end of the snap 285 that is retained in a corresponding recess in the adjacent section to hold the sections together. In some embodiments, the snap 285 may act as a skirt to retain adhesive in a pocket 295. The pocket 295 may provide containment for adhesive applied between the sections (that may have been displaced during assembly of the sections). The additional adhesive in the pocket 295 created by the snap 285 may also provide a stronger bond between the sections. This, along with the manner of assembling the housing cover 290 thereover, may result in some added bulk to the overall probe 101. However, even with these features, the reduction in diameter size for the diaphragms 210, 230 may still result in a thinner diameter probe 101 and housing 100.

While the above embodiment is tailored to reducing housing diameter, multi-diaphragm architecture may be utilized for other enhancements as well. For example, given the cumulative effect on force that results, a multi-diaphragm configuration may be utilized with conventional diameter sizing that does not provide a thinner probe 101. Instead, forces may be driven upward beyond conventionally attainable lbs. without the requirement of increasing pressure beyond industry standards. Alternatively, conventional sizing may be employed with a multi-diaphragm configuration and air pressure reduced while still attaining the same total force and presumed reciprocation rate.

Figure 3:
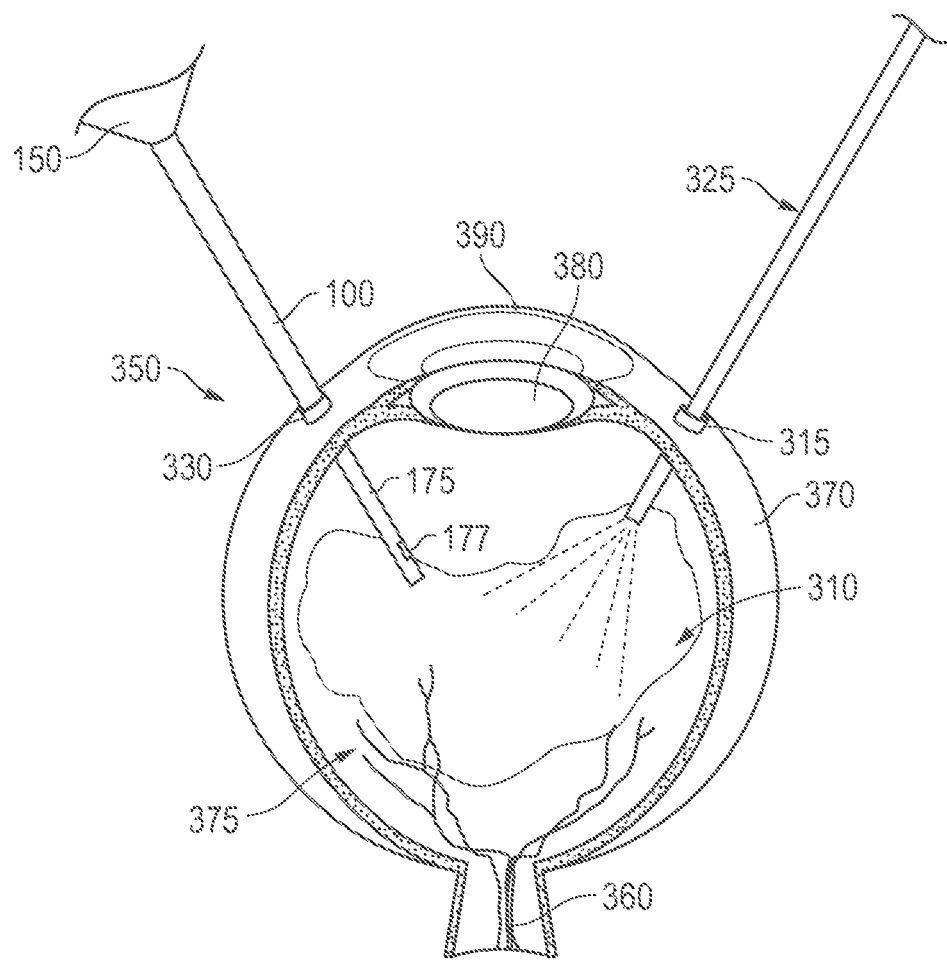
FIG. 3 is a side cross-sectional overview of a patient's eye during a vitrectomy procedure in which the multi-diaphragm vitrectomy probe of FIGS. 1 and 2 is utilized.

Referring now to FIG. 3, a side cross-sectional overview of a patient's eye 350 is shown during a vitrectomy procedure. During this surgical procedure, the vitrectomy probe 101 of FIGS. 1 and 2a is utilized. Specifically, the needle 175 is inserted through a preplaced cannula 330 and directed toward a region 310 where vitreous humor is to be removed. Specifically, as described above, a suction applied to port 177 is used for the uptake of the vitreous humor or other substances. For example, in the procedure illustrated, a hemorrhage may be taking place in the region 310 such that blood is drawn into the port 177 along with the vitreous humor.

As also described above, a cutter is reciprocating within the needle 175 during this delicate procedure. With added reference to FIG. 2a, this means that multiple diaphragms 210, 230 are utilized to simultaneously generate the driving force for the reciprocation. As a result, the diameter of the probe 101 may be thinner for enhanced control and maneuverability. By the same token, reciprocation may be increased for a more fluid-like uptake of the vitreous humor or pressure utilized in driving the reciprocation may even be reduced without any reduction in cut performance.

Continuing with reference to FIG. 3, the surgery illustrated includes the probe 101 and a light instrument 325 reaching into the eye 350 through cannulas 315, 330 positioned in an offset manner at the sclera 370. In this way, the more delicate cornea 390 and lens 380 may be avoided. By the same token, the optic nerve 360 and retina 375 are also quite delicate. Therefore, given that the needle 175 is capable of reaching these delicate features at the back of the eye 350, the thinner probe 101 with enhanced control and maneuverability may be of particular benefit.

Figure 4:
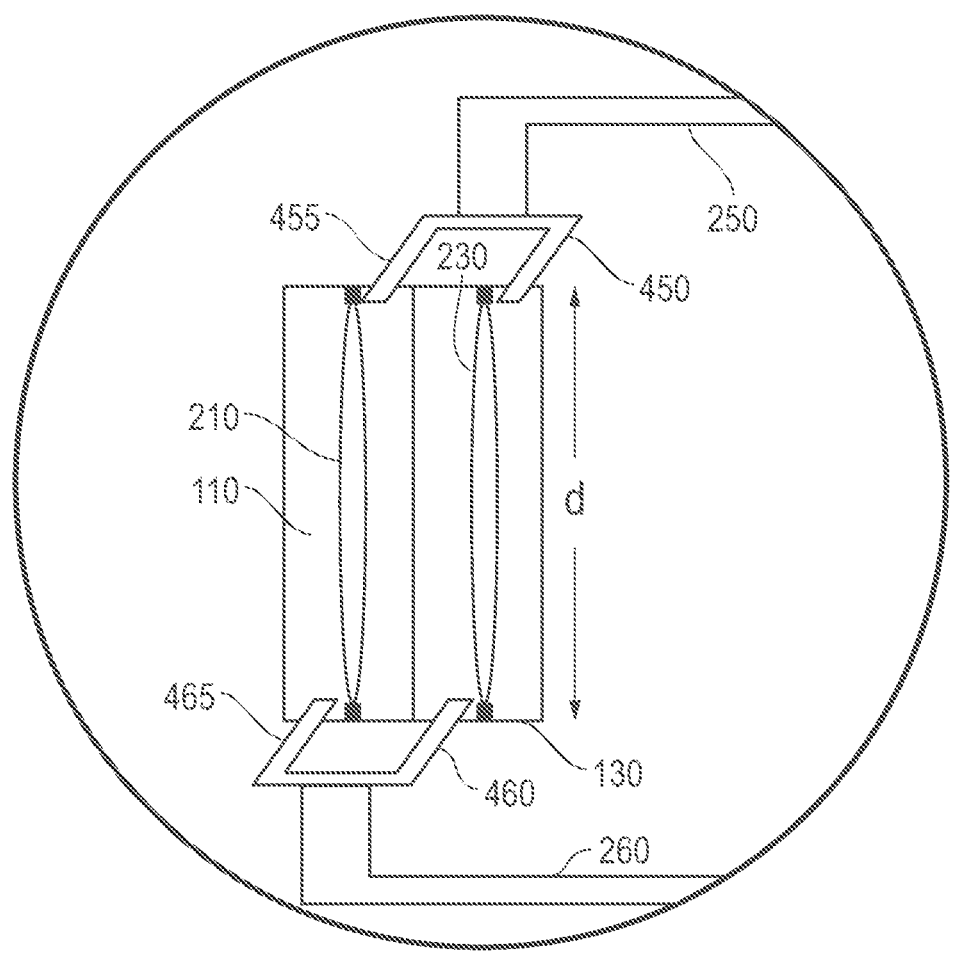

Referring now to FIG. 4, a schematic view of an embodiment of an architectural layout for the air channels 250, 260 of FIG. 2a is illustrated. In this view, the reduced diameter (d) of the diaphragms 210, 230 is apparent with the diaphragms 210, 230 stacked next to each other, at a location that is distal the source of the air pressure. That is, each channel 250, 260 is fed by an air pressure source to the proximal (or right) of the illustration. This means that if the back channel 250 were to linearly and directly interface each diaphragm 230, 210 in a simple fashion without modification, the air within the channel 250 would reach the diaphragms 230, 210 in sequence (first the back diaphragm 230 and then the front 210). The same would be the case for the front channel 260 if not modified from a more linear, direct air path. The end result would likely be continuous misfiring and locking of the reciprocation, possibly rendering the probe ineffective.

As illustrated in FIG. 4, this potential for improper timing and misfiring may be avoided where the flow-paths of the channels 250, 260 are modified from a simple linear architecture to one which ensures that air through either channel 250, 260 reaches either diaphragm 230, 210 at substantially the same time. In the embodiment illustrated, this is achieved with each channel 250, 260 splitting into equidistant subchannels 450, 455 and 460, 465 before reaching the diaphragms 230, 210.

Notice that in the case of the front channel 260 for the embodiment shown, this means that the split into the equidistant front subchannels 460, 465 occurs at a location beyond the back diaphragm 230. In other words, the front channel 260 traverses the location of the back diaphragm 230 before splitting into the subchannels 460, 465 at the middle housing segment 110. This reflects the fact that the diaphragms 230, 210 are stacked and proximal the air source which ultimately needs to reach beyond the locations of the diaphragms 230, 210 in order to target the front sides thereof for reciprocating (to the right in the illustration of FIG. 4). The back channel 250 is tailored to reach the back sides of the diaphragms 230, 210 to impart the opposite stroke of the reciprocation (to the left in the illustration of FIG. 4). Thus, the split to the back subchannels 450, 455 may occur at the proximal housing segment 130 while still keeping the subchannels 450, 455 minimal and equidistant in reaching the back sides of the diaphragms 230, 210. Therefore, proper timing and reciprocation may be better ensured even in a multi-diaphragm configuration.

Figure 5:
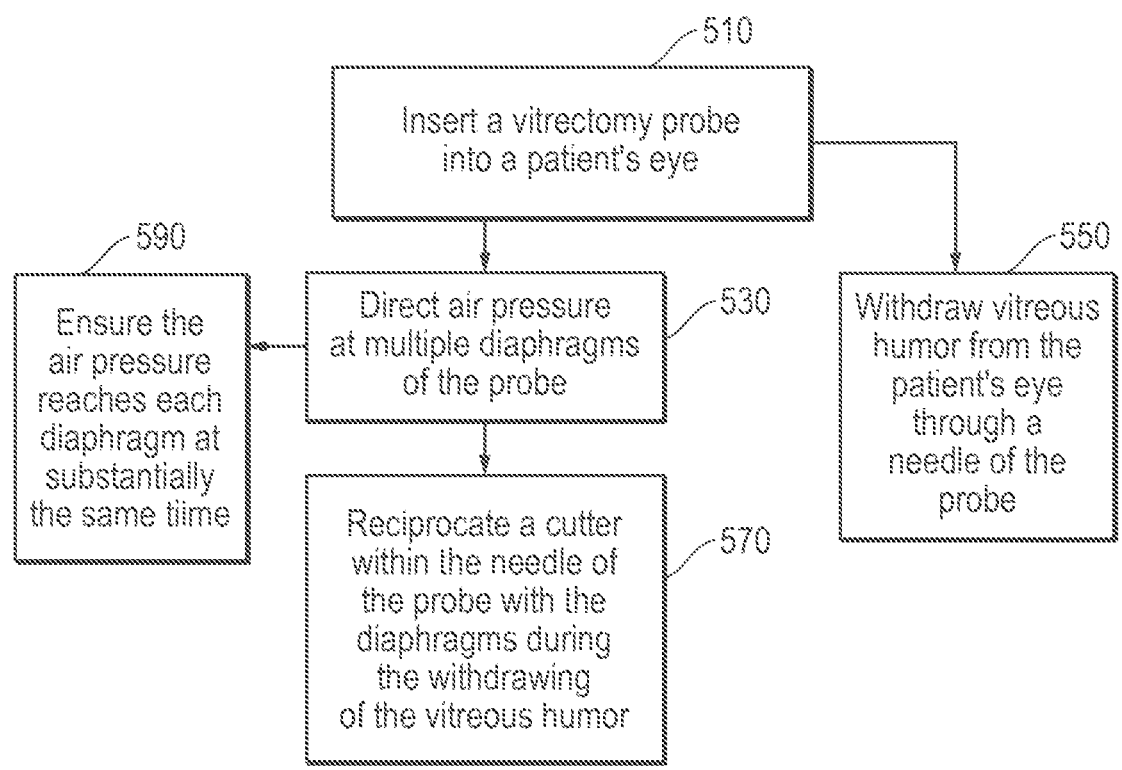
FIG. 5 is a flow-chart summarizing an embodiment of utilizing a multi-diaphragm vitrectomy probe during a vitrectomy procedure.

Referring now to FIG. 5, a flow-chart summarizing an embodiment of utilizing a multi-diaphragm vitrectomy probe during a vitrectomy procedure is illustrated. As with any such procedure, the tool is inserted into the patient's eye as indicated at 510 for withdrawing vitreous humor from the patient's eye by way of a needle of the probe (see 550). For embodiments of the present application, at this time, air pressure is also directed at multiple diaphragms of the probe as noted at 530. Thus, as indicated at 570, a cutter within the needle of the probe is reciprocated by the diaphragms as the vitreous humor is drawn into the needle. Once more, the probe is configured to ensure that air pressure reaches each diaphragm at substantially the same time (see 590).

Embodiments described hereinabove include techniques and configurations that allow for the thinning of a vitrectomy probe. Once more, this may occur without sacrifice to performance or cut rate of the probe. In addition, or alternatively, these same techniques and configurations may be employed to increase force and cut rate or even to decrease pressure utilized during a vitrectomy procedure. Ultimately, the use of a multiple diaphragm configuration allows for flexibility in design while allowing avoidance of sacrifice to vitrectomy probe performance.

The preceding description has been presented with reference to presently described embodiments. However, other embodiments and/or features of the embodiments disclosed but not detailed hereinabove may be employed. Furthermore, persons skilled in the art and technology to which these embodiments pertain will appreciate that still other alterations and changes in the described structures and methods of operation may be practiced without meaningfully departing from the principle and scope of these embodiments. Additionally, the foregoing description should not be read as pertaining only to the precise structures described and shown in the accompanying drawings, but rather should be read as consistent with and as support for the following claims, which are to have their fullest and fairest scope.

The invention claimed is:

1. A vitrectomy probe, comprising:
    a first diaphragm secured about a reciprocating component, the first diaphragm driven in a first direction and an opposite second direction by air reciprocatingly delivered thereto; and
    a second diaphragm secured about the reciprocating component, the second diaphragm driven in the first direction and the opposite second direction by the air reciprocatingly delivered thereto;
    wherein the air is simultaneously delivered to the first diaphragm and the second diaphragm to drive the first diaphragm and the second diaphragm in the first direction at the same time during a first half of the reciprocation, and subsequently, the air is simultaneously delivered to the first diaphragm and the second diaphragm to drive the first diaphragm and the second diaphragm in the second direction at the same time during a second half of the reciprocation.

2. The vitrectomy probe of claim 1, wherein the first diaphragm and the second diaphragm are positioned with a housing having a first diameter of under about 0.60 inches and the first diaphragm and the second diaphragm are of a second diameter of under about 0.30 inches.

3. The vitrectomy probe of claim 2, further comprising:
    an end casing coupled to a first end of the housing for gripping by a surgeon during a vitrectomy procedure; and
    a removable shell coupled to a second end of the housing opposite the first end to serve as an ergonomic support during the procedure.

4. The vitrectomy probe of claim 3, wherein the reciprocating component is an extension tube, the probe further comprising:
    a needle emerging from the end casing to reach into an eye of a patient during the vitrectomy procedure; and
    a cutter coupled to the extension tube for cutting vitreous humor taken into the needle during the vitrectomy procedure.

5. The vitrectomy probe of claim 1, further comprising:
    a front air channel to supply the air to a front of each of the first diaphragm and the second diaphragm to support the driving of the first diaphragm and the second diaphragm in the first direction, the first direction being a distal direction; and
    a back air channel to supply the air to a back of each of the first diaphragm and the second diaphragm to support the driving of the first diaphragm and the second diaphragm in a second direction, the second direction being a proximal direction.

6. The vitrectomy probe of claim 5, wherein the front air channel is split into equidistant subchannels to ensure that the supply of the air to the front of the first diaphragm and the second diaphragm reaches each of the first diaphragm and the second diaphragm simultaneously and the back air channel is split into equidistant subchannels to ensure that the supply of the air to the back of the first diaphragm and the second diaphragm reaches each of the first diaphragm and the second diaphragm simultaneously.

7. A segmented housing assembly for incorporation into a vitrectomy probe, the housing assembly comprising:
    a distal segment and a middle segment to accommodate a first diaphragm secured about a reciprocating component therebetween, the first diaphragm driven in a first direction and an opposite second direction by air reciprocatingly delivered thereto; and
    a proximal segment adjacent the middle segment to accommodate a second diaphragm secured about the reciprocating component therebetween, the second diaphragm driven in the first direction and the opposite second direction by the air reciprocatingly delivered thereto;
    wherein the air is simultaneously delivered to the first diaphragm and the second diaphragm to drive the first diaphragm and the second diaphragm in the first direction at the same time during a first half of the reciprocation, and subsequently, the air is simultaneously delivered to the first diaphragm and the second diaphragm to drive the first diaphragm and the second diaphragm in the second direction at the same time during a second half of the reciprocation.

8. The segmented housing assembly of claim 7, wherein the segments are attachable to one another by one of a snap fit and mechanical keying, wherein the at least one of the snap fit and mechanical keying further define a pocket to contain adhesive between the segments and the at least one of the snap fit and mechanical keying.

9. The segmented housing assembly of claim 7, further comprising:
    a front air channel to supply the air to a front of each of the first diaphragm and the second diaphragm to support the driving of the first diaphragm and the second diaphragm in the first direction, the first direction being a distal direction, the front air channel comprising equidistant subchannels to facilitate the air reaching the front of each of the first diaphragm and the second diaphragm simultaneously; and
    a back air channel to supply the air to a back of each of the first diaphragm and the second diaphragm to support the driving of the of the first diaphragm and the second diaphragm in a second direction, the second direction being a proximal direction, the back air channel comprising equidistant subchannels to facilitate the air reaching the back of each of the first diaphragm and the second diaphragm simultaneously.

10. The segmented housing assembly of claim 9, wherein the equidistant subchannels of the front air channel emerge from a split at about a location of the middle segment and the equidistant subchannels of the back air channel emerge from a split at about a location of the proximal segment.

* * * * *